US012364788B2

(12) United States Patent
Drago et al.

(10) Patent No.: US 12,364,788 B2
(45) Date of Patent: Jul. 22, 2025

(54) IMPLANTABLE PASTE AND ITS USE

(71) Applicant: BonAlive Biomaterials Oy, Turku (FI)

(72) Inventors: Lorenzo Drago, Monza (IT); Carlo Luca Romano, Milan (IT); Jimmy Lucchesi, Turku (FI); Fredrik Ollila, Turku (FI)

(73) Assignee: BonAlive Biomaterials Oy, Turku (FI)

( * ) Notice: Subject to any disclaimer, the term of this patent is extended or adjusted under 35 U.S.C. 154(b) by 126 days.

(21) Appl. No.: 15/125,932

(22) PCT Filed: Mar. 16, 2015

(86) PCT No.: PCT/EP2015/055392
§ 371 (c)(1),
(2) Date: Sep. 13, 2016

(87) PCT Pub. No.: WO2015/140088
PCT Pub. Date: Sep. 24, 2015

(65) Prior Publication Data
US 2017/0072098 A1 Mar. 16, 2017

(30) Foreign Application Priority Data
Mar. 17, 2014 (EP) .................................. 14160184

(51) Int. Cl.
| A61L 27/32 | (2006.01) |
| A61L 24/00 | (2006.01) |
| A61L 27/46 | (2006.01) |

(52) U.S. Cl.
CPC ........... *A61L 27/32* (2013.01); *A61L 24/0084* (2013.01); *A61L 27/46* (2013.01); *A61L 2430/02* (2013.01)

(58) Field of Classification Search
None
See application file for complete search history.

(56) References Cited

U.S. PATENT DOCUMENTS

| 5,290,558 A | 3/1994 | O'Leary et al. |
| 6,190,643 B1 * | 2/2001 | Stoor ........................ A61K 8/25 424/49 |
| 2008/0226688 A1 | 9/2008 | DePaula |
| 2009/0324668 A1 | 12/2009 | Kangasniemi et al. |
| 2012/0164187 A1 | 6/2012 | Ollila et al. |

FOREIGN PATENT DOCUMENTS

| AU | 2004272072 | | 3/2005 | |
| CA | 2582551 C | * | 6/2012 | ......... A61L 27/3847 |
| EP | 2322134 | | 5/2011 | |
| EP | 2322134 A1 | * | 5/2011 | ............ A61K 6/0008 |
| JP | 2013510611 A1 | | 3/2013 | |
| KR | 20080081290 A | | 9/2008 | |

OTHER PUBLICATIONS

Lepparanta et al. Antibacterial effect of bioactive glasses on clinically important anaerobic bacteria in vitro, J Mater Sci: Mater Med (2008) 19:547-551. (Year: 2008).*
Christensen et al., "Adherence of Coagulase-Negative Staphylococci to Plastic Tissue Culture Plates: a Quantitative Model for the Adherence of Staphlococci to Medical Devices," 22 J. Clin. Microbiol. 996 (1985).
Drago et al., "Bioactive Glass BAG-S53P4 for the Adjunctive Treatment of Chronic Osteomyelitis of the Long Bones: An In Vitro and Prospective Clinical Study," 13 BMC Infectious Diseases 584 (2013).
Hench, "Bioactive Ceramics: Theory and Clinical Applications", 7 Bioceramics 3-14 (Anderson & Yli-Urpo ed. 1994).
"Second Consensus Conference on Definitions in Bioceramics", Biomaterial-Tissue Interfaces (Williams, Black & Doherty eds., Elsevier 1991).
Vuorenoja et al., "Detection of *Streptococcus pneumoniae* Carriage by the Binax NOW Test With Nasal and Nasopharyngeal Swabs in Young Children," 31 Eur. J. Clin. Microbiol. Infect. Dis. 703 (2012).
"Definitions in Biomaterials," 4 Progress in Biomedical Engineering (Williams ed., Elsevier 1987).
Lepparanta et al., "Antibacterial Effect of Bioactive Glasses on Clinically Important Anaerobic Bacteria in Vitro," 19 J. Materials Sci. 547 (2007).
Vallet-Regi et al., "Bioceramics: From Bone Regeneration to Cancer Nanomedicine," 23 Adv. Mater. 5177 (2011).
Coraca-Huber et al., "Efficacy of Antibacterial Bioactive Glass S53P4 Against *S. aureus* Biofilms Grown on Titanium Discs in Vitro," 32 J. Orthro. Res. 175 (2014).

(Continued)

*Primary Examiner* — Carlos A Azpuru
*Assistant Examiner* — Casey S Hagopian
(74) *Attorney, Agent, or Firm* — Timothy H. Van Dyke; Wolter Van Dyke Davis, PLLC

(57) ABSTRACT

The present invention relates to an implantable paste comprising bioactive glass powder having a size distribution of 0.5-45 μm, bioactive glass granules having a size distribution between 100 and 4000 μm, low molecular weight polyethylene glycol having a molecular weight range of 200-700 g/mol, medium molecular weight polyethylene glycol having a molecular weight range of 700-2500 g/mol, high molecular weight polyethylene glycol having a molecular weight range of 2500-8000 g/mol and glycerol. The composition of the bioactive glass is 45-55 weight-% of $SiO_2$, 20-25 weight-% of $Na_2O$, 18-25 weight-% of CaO and 3-6 weight-% of $P_2O_5$, and the molecular weight of the low molecular weight polyethylene glycol and of the medium molecular weight polyethylene glycol differ from each other by at least 80 g/mol and that the molecular weight of the medium molecular weight polyethylene glycol and of the high molecular weight polyethylene glycol differ from each other by at least 300 g/mol.

10 Claims, No Drawings

(56) References Cited

OTHER PUBLICATIONS

McAndrew et al., "Through the Looking Glass; Bioactive Glass S53P4 (BonAlive) in the Treatment of Chronic Osteomyelitis," 182 Ir. J. Med. Sci 509 (2013).
Notice of Rejection in Japanese Application 2016-555744.
Munukka et al., "Bactericidal Effects of Bioactive Glasses on Clinically Important Aerobic Bacteria," 19 J. Mater. Sci.: Mater. Med 27 (2007).
Search report in Russian patent application 2016140417 (dated Aug. 17, 2018) with English translation.

* cited by examiner

IMPLANTABLE PASTE AND ITS USE

The present invention relates to an implantable paste comprising bioactive glass, for use as an implant or coating of an implant.

BACKGROUND OF THE INVENTION

Bioactive glass is a known bioactive and biocompatible material. For decades, bioactive glasses have been investigated as bone filling materials that can bond with bone, even chemically. Recent discoveries of the superior qualities of bioactive glasses have made the materials far more interesting for these applications. Certain bioactive glasses are commercially sold under the trade names of e.g. BonAlive®, NovaBone® and Biogran®. Bioactive glasses have been used in different forms for medical applications, such as granules and plates for orthopaedic and cranio-maxillofacial bone cavity filling and bone reconstruction.

The main benefits of using bioactive glass as a bone graft substitute is that harvesting of the bone grafts from a secondary site can be avoided. Within a certain composition range bioactive glasses stimulate bone growth and show bacterial-growth inhibiting properties.

In order for the glass to be bioactive and have the above-mentioned properties the glass needs to dissolve and to have a certain dissolution rate as well as have certain composition. The relationship between the composition and the bioactivity has been described in Hench L. Bioactive ceramics: Theory and clinical applications. Bioceramics 1994; 7:3-14 in a way that gives a person skilled in the art sufficient tools to design a bioactive glass.

One factor influencing the dissolution rate and therefore the total degradation time of the glass particles is the particle size, or the surface area to volume ratio (A/V). In other words the smaller the particle the higher the A/V ratio and the faster the dissolution and the shorter the total degradation time. For example, the commercially available glass 45S5/Bioglass® is available in a size range from 90-710 µm and it is claimed to dissolve in the body in less than a year. Glass S53P4, sold under the trade name BonAlive®, has a chemical composition of 53 weight-% of $SiO_2$, 23 weight-% of $Na_2O$, 20 weight-% of CaO and 4 weight-% of $P_2O_5$, and it is a clearly slower dissolving glass than the 45S5 glass that has a composition of 45 weight-% of $SiO_2$, 24.5 weight-% of $Na_2O$, 24.5 weight-% of CaO, and 6 weight-% of $P_2O_5$.

In order to enhance the use and to broaden the surgical scope of bioactive glass, mouldable paste or putty types of compositions have been developed. In an ideal case, the putty formulation should be easy to dose, handle and directly administer to the bone defect without risk of cross-contamination, spillage or excess dosage. In practice, physicians have used their hands in dosing and shaping of putty, and fingers and/or spatula or similar for filling the bone cavities. However, such a formulation possesses a number of practical disadvantages due to e.g. contamination risks during handling, which is not optimal for the patient or the physician.

One synthetic putty/paste formulation is known from US 2008/0226688 and is commercially known as NovaBone® Putty. The document describes a bone void filler type of paste or putty i.e. a sterile formable implant composition for application to a bone defect site comprising bioactive glass particles in an aqueous carrier solution. The bioactive glass particles are added to a viscous carrier at a concentration ranging from about 68% to about 76% (wt/wt). The carrier comprises a mixture of glycerol and medium molecular weight polyethylene glycol (PEG) ranging from 24% to 32% (wt/wt) with the ratio of glycerol to polyethylene glycol ranging from about 45:55 to about 65:35.

In addition to fully synthetic bone void filler putties or pastes, certain semi-synthetic mixtures in the form of putty or paste formulations, such as mixtures of allograft bones, demineralised bone matrix and bovine collagen/hydroxyapatite, have been in wide use and are known in the art. However, such allograft formulations possess a number of disadvantages of which the risk of transmission of disease is the largest disadvantage and can never be fully excluded.

Furthermore, infections of prosthetic joints (PJIs) and other non-biological implants are an important concern for the healthcare system, and are related with a lot of inconvenience for patients, such as prolonged hospitalization, additional surgery associated with higher risk of complications and long-time antimicrobial treatment. Despite of the relatively low incidence of PJIs (1-2%), the associated economic impact remains enormous. A wide range of microorganisms are able to produce biofilm on prosthetic materials, causing in many cases, a fatal course of the therapy. *Staphylococcus aureus*, coagulase negative staphylococci and gram-negative rods are the most commonly involved pathogens in PJIs.

The first step in the PJIs pathogenesis is the adherence of bacterial cells to the implant, followed by the formation of a biofilm matrix. A biofilm is a matrix-enclosed microbial population characterized by cell to cell adhesion between microorganisms and the non-biological surface. Biofilm formation is an ancient and integral component of the prokaryotic cell cycle and an important factor for bacterial survival in the environment. The common feature of biofilm-related infections is their intrinsic resistance to host immunity, conventional antimicrobial agents and biocides. Bacteria enclosed in biofilm structures are in fact known to tolerate levels of antibiotics 10 to 1000 times higher than the minimum inhibitory concentrations of the corresponding planktonic form.

A yet further problem related to bacterial infections in general is the ability of the bacteria to become resistant to antibiotics. It is not a recent phenomenon, but it is a critical health issue today. Over several decades, to varying degrees, bacteria causing common infections have developed resistance to each new antibiotic, and antimicrobial resistance has evolved to become a worldwide health threat according to the Center for Disease Control and Prevention in the US and the World Health Organization.

Indeed, infections from resistant bacteria are now too common, and some pathogens have even become resistant to multiple types or classes of antibiotics. Today antibiotic resistance is encountered in most hospitals and it has been estimated that 70% of all bacteria will be resistant towards antibiotics by 2020. The in-vitro bacterial growth inhibition activity of BAG S53P4 against methicillin resistant *S. aureus* (MRSA), methicillin resistant *Staphylococcus epidermidis* (MRSE), *Pseudomonas aeruginosa* and *Acinetobacter baumannii* that were isolated from patients affected by chronic osteomyelitis has been demonstrated (Drago L, Romanò D, De Vecchi E, et al. Bioactive glass BAG-S53P4 for the adjunctive treatment of chronic osteomyelitis of the long bones. An in vitro and prospective clinical study. *BMC Infect. Dis.* 10, 13:584 (2013)). However, although it is known that small particles of this bioactive glass have an antibacterial effect, their interaction with other components of a mixture useful in practice is not known.

Document "Antibacterial effect of bioactive glasses on clinically important anaerobic bacteria in vitro", J. Mat. Sc.:

Mat. in Medicine, Vol 19, no. 2, 10 Jul. 2007 discloses that powder of bioactive glass S53P4 with a particle size of equal or less than 45 micrometers has a good antibacterial effect. Document EP 2322134 of the present applicant discloses implantable pastes comprising different types of polyethylene glycols and bioactive glass spheres. As shown below, these pastes are however not antibacterial.

DEFINITIONS

The terms used in this application, if not otherwise defined, are those agreed on at the consensus conference on biomaterials in 1987 and 1992, see Williams, D F (ed.): Definitions in biomaterials: Proceedings of a consensus conference of the European Society for Biomaterials, Chester, England. Mar. 3-5, 1986. Elsevier, Amsterdam 1987, and Williams D F, Black J, Doherty P J. Second consensus conference on definitions in biomaterials. In: Doherty P J, Williams R L, Williams D F, Lee A J (eds). Biomaterial-Tissue Interfaces. Amsterdam: Elsevier, 1992.

In this application, by bioactive material is meant a material that has been designed to elicit or modulate biological activity. Bioactive material is often surface-active material that is able to chemically bond with the mammalian tissues.

The term resorbable in this context means that the material is disintegrated, i.e. decomposed, upon prolonged implantation when inserted into mammalian body and when it comes into contact with physiological environment. Especially, the term resorbable glass means silica-rich glass that does not form a hydroxyl-carbonate apatite layer on its surface when in contact with physiological environment. Resorbable glass disappears from the body through resorption and does not significantly activate cells or cell growth during its decomposition process.

By biomaterial is meant a material intended to interface with biological systems to evaluate, treat, augment or replace any tissue, organ or function of the body. By biocompatibility is meant the ability of a material used in a medical device to perform safely and adequately by causing an appropriate host response in a specific location. By resorption is meant decomposition of biomaterial because of simple dissolution. By composite is meant a material comprising at least two different constituents, for example an organic polymer and a ceramic material, such as glass.

OBJECTS AND SUMMARY OF THE INVENTION

An object of the present invention is to provide compositions useful as bone void fillers that are easy and safe to handle and that have the desired properties as to the bone filling effect, while at the same time being antibacterial. Another object of the invention is to provide a composition that is useful in preventing the formation of biofilm on the surface of an implant. An object of the invention is thus also to provide a material for use in implant surgery to prevent infections locally. A yet further object of the invention is to provide a material for which bacteria will not become resistant.

The present invention relates to an implantable paste comprising bioactive glass granules having a size distribution of 0.5-45 μm and bioactive glass granules having a size distribution of 100-4000 μm. The composition of the bioactive glass is 45-55 weight-% of $SiO_2$, 20-25 weight-% of $Na_2O$, 18-25 weight-% of CaO and 3-6 weight-% of $P_2O_5$. The paste further comprises low molecular weight polyethylene glycol having a molecular weight range of 200-700 g/mol, medium molecular weight polyethylene glycol having a molecular weight range of 700-2500 g/mol, high molecular weight polyethylene glycol having a molecular weight range of 2500-8000 g/mol and glycerol, with the proviso that the molecular weight of the low molecular weight polyethylene glycol and of the medium molecular weight polyethylene glycol differ from each other by at least 80 g/mol and that the molecular weight of the medium molecular weight polyethylene glycol and of the high molecular weight polyethylene glycol differ from each other by at least 300 g/mol.

The invention also relates to the use of a paste according to this invention in manufacturing an implant for use in bone formation. The invention yet further relates to the use of a paste according to this invention in coating an implant. The invention still relates to an implant coated with a paste according to this invention.

DETAILED DESCRIPTION OF THE INVENTION

The present invention relates to an implantable paste comprising
(a) bioactive glass powder having a size distribution of 0.5-45 μm
(b) bioactive glass granules having a size distribution between 100 and 4000 μm,
(c) low molecular weight polyethylene glycol having a molecular weight range of 200-700 g/mol,
(d) medium molecular weight polyethylene glycol having a molecular weight range of 700-2500 g/mol,
(e) high molecular weight polyethylene glycol having a molecular weight range of 2500-8000 g/mol and
(f) glycerol,
wherein the composition of the bioactive glass is 45-55 weight-% of $SiO_2$, 20-25 weight-% of $Na_2O$, 18-25 weight-% of CaO and 3-6 weight-% of $P_2O_5$, with the proviso that the molecular weight of the low molecular weight polyethylene glycol and of the medium molecular weight polyethylene glycol differ from each other by at least 80 g/mol and that the molecular weight of the medium molecular weight polyethylene glycol and of the high molecular weight polyethylene glycol differ from each other by at least 300 g/mol.

The present invention thus provides a composition that is osteoconductive, bioactive, antibacterial and mouldable. The paste comprises bioactive glass granules in a viscous organic carrier solution or matrix. The paste is thus composed of calcium-phosphorous-sodium-silicate particles mixed with a synthetic binder composed of polyethylene glycol that acts as a temporary binding agent for the particles. The particles and the binder are typically provided as a premixed cohesive material. On implantation, the binder is absorbed to permit tissue infiltration between the particles and permit the normal healing process of bone associated with the particles (resorption of bioactive glass and bone regeneration). Once the binder is absorbed shortly after the implantation, it leaves behind only the bioactive glass particles. All of these components are well known and widely used and tolerated in medical, pharmaceutical and cosmetic fields as well as in foods and beverages.

At least part of the above-mentioned objects, if not all, is thus achieved by the present invention and its various embodiments. Indeed, when a powder of small bioactive particles is combined with a mixture of polyethylene glycols, the resulting material surprisingly has antibacterial effect, while at the same time improves bone ingrowth.

The patent EP 2322134 discloses a similar composition, comprising bioactive glass spheres and a mixture of different polyethylene glycols (low, medium and high molecular weight PEGs). It has however been observed that such composition, where the bioactive glass is BonAlive® bioactive glass, does not have a significant antibacterial effect. On the other hand, the BonAlive® bioactive glass alone has been proven to have antibacterial effect irrespective of its particle size, even against antibiotic resistant bacteria. However, a powder of small bioactive particles (average diameter below 45 µm) cannot be incorporated in mammalian tissues as such (i.e. alone) since its reaction rate is too high and may even be dangerously high. It would also not promote bone growth due to its high reaction rate.

When compared to a bioactive glass powder of similar particle size, the present material, including the polyethylene glycols, has the further advantage that it can be applied through a tube, allowing its use also in minimal invasive surgery. The material is viscous and thus fills the defect in a controlled, gradual manner, in contrast to free-flowing dry powder. It is thus possible to control the even distribution of the paste to the defect.

It may be also possible to combine the bioactive glass in the form of small particle size powder to larger granules, which would have an influence on both the flow properties of the material as well as its bone ingrowth properties. The choice of the polyethylene glycols may also be tailored to meet the needs for flow properties.

In the present description, the abbreviation wt-% stands for weight percentage, and is typically expressed as a weight percentage of the total weight. The molecular weight is the mean molecular weight, which is here the number average molecular weight, and is expressed as g/mol. The size distribution of the bioactive glass particles is determined by sieving.

By granules, it is meant particles that have any regular or irregular shape other than spheres. The powder of bioactive glass is also made of granules.

According to a preferred embodiment, the paste also comprises (g) therapeutically active agent.

According to an embodiment, the bioactive glass granules have a size distribution of 500-800 µm. According to another embodiment, the bioactive glass granules have a size distribution of 100-350 µm. According to yet another embodiment, the bioactive glass granules have a size distribution of 315-500 µm. According to another embodiment, the bioactive glass granules have a size distribution between 1000 and 2000 µm. The composition may for example comprise the bioactive glass in powder form and granules having a size distribution of 315-500 µm. Such a composition could be useful for example for dental surgery. Another possible combination is the powder and granules having a size distribution of 500-800 µm. This composition could be useful for craniomaxillofacial and hand surgery. A further possible combination is the powder with granules having a size distribution of 1000-2000 µm. This composition could be useful for orthopaedic, trauma and spine surgery.

The composition may thus comprise bioactive glass in powder form, i.e. in granules having a size distribution of 1-44 µm. The size distribution can be for example from 1, 5, 10, 15, 20, 25, 30, 35 or 40 µm up to 5, 10, 15, 20, 25, 30, 35, 40 or 45 µm. The composition additionally comprises larger granules, which can have a size distribution of for example 100-350 µm or 100-200 µm or 150-250 µm or 200-300 µm or 250-350 µm. The size distribution of these larger granules may also be for example 315-500 µm or 350-500 µm or 400-500 µm. The size distribution of the larger granules may even further be for example 500-800 µm or 500-700 µm or 550-800 µm or 600-800 µm or 650-750 µm. The size distribution can also, in some embodiments, be for example 1000-2000 µm or 1000-1500 µm or 1300-1800 µm or 1500-2000 µm or 2000-3150 µm. The size distribution of the glass granules is determined by sieving.

The size distribution of the glass granules may also be for example from 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1500, 1600, 1700, 1800, 1900, 2000, 2100, 2200, 2300, 2400, 2500, 2600, 2700, 2900, 3000 or 3150 µm up to 150, 200, 250, 300, 350, 400, 450, 500, 550, 600, 650, 700, 750, 800, 850, 900, 950, 1000, 1050, 1100, 1150, 1200, 1250, 1300, 1350, 1400, 1500, 1600, 1700, 1800, 1900, 2000, 2100, 2200, 2300, 2400, 2500, 2600, 2700, 2900, 3000, 3100, 3150, 3200, 3300, 3400, 3450, 3550, 3600, 3700, 3800, 3900 or 4000 µm.

Polyethylene glycols (PEG), also known as polyethylene oxides, contain the repeating unit ($-CH_2CH_2O-$) and are prepared by stepwise addition of ethylene oxide to a compound containing a reactive hydrogen atom. Polyethylene glycols are prepared by addition of ethylene oxide to ethylene glycol to produce a difunctional polyethylene structure $HO(CH_2CH_2O)_nH$, where n is an integer of varying size depending on the molecular weight of polyethylene glycol.

Polyethylene glycols used in the present invention are generally linear polyethylene glycols i.e. having molecular weight of 100 to 8000 g/mol. Also branched and stars shaped polyethylene glycols can be used to reduce or further tailor the viscosity of the paste. Polyethylene glycols are typically named as PEG with a figure, the figure denoting the mean molecular weight in g/mol. Thus, PEG 400 means polyethylene glycol having mean molecular weight of 400 g/mol and PEG 2000 means polyethylene glycol having mean molecular weight of 2000 g/mol.

Polyethylene glycols (PEGs) are used to form a paste-like material by binding and wetting the bioactive glass particles. In order to achieve suitable viscosity of the paste, at least two PEGs should be mixed together. When choosing the appropriate molecular weights for the PEGs, one should bear in mind that low molecular weight PEG (<600 g/mol) is liquid at room temperature but higher molecular weight PEGs are waxy or solids.

In order to have a paste that remains paste-like in its use temperatures (room and body temperatures), at least three PEGs are mixed together, typically in elevated temperatures. As higher molecular weight PEGs are crystalline materials, their use will raise the upper limit of the use temperature of the paste as well as increase the paste's viscosity and prevent the sedimentation of bioactive glass particles in room temperature during storage. In order to decrease the lower limit of the use temperature, i.e. widening the use temperature range, low molecular weight PEGs are useful for avoiding solidification i.e. hardening of the paste at lower temperatures, as high molecular weight PEGs tend to crystallize in low temperatures.

If only one molecular weight waxy or solid PEG would be used, the use temperature would be too narrow for practical uses. PEG 600 (i.e. polyethylene glycol having 600 g/mol as mean molecular weight) shows a melting range of about 17 to 22° C., so it may be liquid at room temperature but pasty at lower ambient temperatures, while PEGs with 800 to 2000 mean molecular weight are pasty materials with a low melting range. Above a molecular weight of 3000, the polyethylene glycols are typically solids.

Glycerol, i.e. propane-1,2,3-triol, is commonly called glycerin or glycerine. It is a colourless, odourless, viscous liquid that is widely used in pharmaceutical formulations. Glycerol may be added to the paste to improve its smoothness and to provide further lubrication by enhancing the thermal and viscosity properties due to the physical interactions between PEGs and glycerol. PEGs and glycerol are compatible with each other.

PEG 400 is miscible in all proportions to glycerol but the dissolving power and the solubility of PEGs in glycerol decreases as the molar mass increases. However, both of these properties can be improved by moderate heating and substances that dissolve at room temperature in PEG 400 are soluble to roughly the same extent in molten PEG 4000 (i.e. at a temperature of 60-70° C.).

According to one embodiment of the invention, the total amount of bioactive glass is 50-80 wt-% of the total weight of the paste. The amount of bioactive glass particles having a size distribution of 0.5-45 µm (a) is 10-30 wt-% of the total weight of the bioactive glass and the amount of bioactive glass granules having a size distribution of 100-4000 µm, (b) is 90-70 wt-% of the total weight of the bioactive glass in the paste.

Preferably, the total amount of polyethylene glycols is 20-50 wt-% of the total weight of the paste. For example, the amount of low molecular weight PEG (c) is 2-15 wt-% and amount of medium molecular weight PEG (d) is 8-48 wt-% of the total weight of the paste. The amount of high molecular weight PEG (e) is 1-10 wt-% of the total weight of the paste.

In the embodiment where glycerol is used, its amount is up to 10 wt-% of the total weight of the paste. Some suitable pastes have the following composition:

| | |
|---|---|
| PEGs (c + d + e) | 23-45 wt-%, |
| glycerol (f) | 0-10 wt-% and |
| bioactive glass (a + b) | 55-67 wt-%. |

Some preferable pastes have the following composition range:

| | |
|---|---|
| low molecular weight PEG (c) | 4-10 wt-% |
| medium molecular weight PEG (d) | 13-18 wt-% |
| High molecular weight PEG (e) | 1-8 wt-% |
| Glycerol (f) | 8-10 wt-% |
| Small bioactive glass granules (a) | 8-12 wt-% |
| Larger bioactive glass granules (b) | 48-52 wt-%. |

According to an embodiment of the invention, the amount of therapeutically active agent (g) is up to 30 wt-% of the total weight of the paste. The therapeutically active agent can be selected from the group consisting of growth factors, proteins, peptides, antibiotics, mucopolysaccharides i.e hyaluronic acid, stem cells of non-human origin (i.e. excluding human stem cells), peroxides, and mixtures thereof, and be used to promote bone growth or to have a further antimicrobial such as antibacterial effect. It is however to be noted that the present material is effective also in the absence of antibiotics.

In an embodiment of the invention, the composition of the bioactive glass is 45-54 weight-% of $SiO_2$, 22-25 weight-% of $Na_2O$, 19-25 weight-% of CaO and 3.5-6 weight-% of $P_2O_5$. In another embodiment of the invention, the composition of the bioactive glass is 53 weight-% of $SiO_2$, 23 weight-% of $Na_2O$, 20 weight-% of CaO and 4 weight-% of $P_2O_5$. Such bioactive glass is also known as S53P4 and sold under the trade name of BonAlive®. This embodiment provides a fast in vivo dissolving binder composition that permits the normal healing process of bone associated with S53P4 granules (resorption of bioactive glass and bone regeneration) and powder. Due to the slow dissolution rate of S53P4 bioactive glass chemical composition and particle size the long term bone growth effect will be naturally achieved. According to another embodiment, the composition of the bioactive glass is 45 weight-% of $SiO_2$, 24.5 weight-% of $Na_2O$, 24.5 weight-% of CaO and 6 weight-% of $P_2O_5$. This bioactive glass is also known as 45S5 and sold under the trade name of NovaBone®.

Pastes comprising all the ingredients at the extreme ends of the ranges may not necessarily give optimal flow and product properties. For example, combining a high molecular weight PEG in high concentration without sufficient low molecular weight PEG and/or glycerol may give high viscose product, which is not suitable for injection at room or body temperatures. A person skilled in the art will however be able to find out the ideal ratio of ingredients through some easy experimentation, for each set of desired properties. Some examples of suitable combinations are also given in the Experimental part below.

The invention also provides a method of producing a mouldable bone void filler paste having antimicrobial properties, which includes melting and mixing the raw materials in controlled conditions, as well as cooling, packaging and conditioning of the final products.

The paste is typically produced by mixing and/or melting the ingredients together in a batch mixer at a temperature of 25 to 95° C. under a protective gas or vacuum or in atmospheric conditions for 5 to 60 min. The mixture is then cooled to 25-45° C. and transferred to an applicator and/or stored for further use. Alternatively, the mixing, melting and/or transferring can be done by using any type of mixing equipment e.g. an open or closed batch mixer, continuous stirring tank reactor or mixer, extruder, injection moulding machine, tube reactor or other standard melt processing or melt mixing equipment known in the field.

The invention also provides a use of the present paste in manufacturing an implant for use in bone formation, such as at a bone defect site, i.e. as a bone void filler paste. The invention further provides a use of the present paste for coating an implant. Indeed, it has been determined that the present paste has an ability to prevent and treat biofilm forming on the surface of implants. It can also be used in the treatment of prosthetic infections related to biofilm, since it has antibacterial efficacy against the most problematic bacteria of prosthetic infections. Furthermore, the paste according to this description can be used for treatment of wounds, where the paste is applied on an open wound and covered.

The invention still provides an implant coated with the present paste. The implant can be for example a hip implant, a knee implant or any other prosthetic joint, or any other implant incorporated into mammals. The implant is coated with the present paste prior to implantation into the human or animal body.

In addition, the invention provides antimicrobial bone growth promoting compositions comprising the above mentioned formulation with active agents. The active agent may be any pharmaceutically active agent for human or animal use.

Different embodiments of the present invention will now be described in more detail in the following Experimental part.

EXPERIMENTAL PART

Generalized Manufacturing Method for Putty

Glycerol and PEG 400 was added to a heated reactor (60° C.) using 100 RPM (rotations per minute) mixing speed followed by addition of PEG 1500 and PEG 3000. PEGs were supplied by Clariant and glycerol was supplied by Uniqema or Sigma-Aldrich. Granules of bioactive glass were added to the molten mixture and mixed until the mixture was homogeneous. The obtained putty was cooled down to room temperature (RT) under mixing and the vessel was discharged, packed and stored in a desiccator for further use and testing.

Antimicrobial Activity of Reference Bioactive Glasses

The ability of bioactive glass alone and with a matrix as described in this description to kill bacteria was tested as follows, as comparative examples. The bacteria used in the test are listed in Table 1. MetR stands for Methicillin-resistant. The various glasses tested are listed in Table 2. Glass S53P4 and BonAlive® glass have the same composition, as described above.

| BonAlive® Putty composition | |
|---|---|
| Glycerol | 16 g |
| PEG 400 | 12.8 g |
| PEG 1500 | 25.6 g |
| PEG 3000 | 9.6 g |
| 500-800 µm S53P4 granules | 76.8 g |
| 90-425 µm S53P4 spheres | 19.2 g |

PEG stands for polyethylene glycol and the figure behind denotes the average molecular weight in g/mol. The same mixture of glycerol, PEG 400, PEG 1500 and PEG 3000 (i.e. the paste-like binder) was used for the reference samples Putty 1 to Putty 6 as for BonAlive® Putty.

TABLE 1

Bacterial strains

| Bacteria | Description |
|---|---|
| Staphylococcus aureus, ATCC 29213 | Gram positive cocci, part of the human skin flora, found in the nose and on skin |
| Staphylococcus aureus MetR, ATCC 43300 | Gram positive cocci |
| Staphylococcus epidermidis, ATCC 14990 | Gram positive cocci, part of the human skin flora & mucosa |
| Pseudomonas aeruginosa, ATCC 27853 | Gram negative, rod-shaped, opportunistic pathogen, secretes a variety of pigments, creates dark, gellish mats during growth |

TABLE 2

Tested products, controls and reference materials

| Comparative example | Product | Description |
|---|---|---|
| 1 | BonAlive® 0.5-0.8 | Granule size 0.5-0.8 mm, gamma sterilized |
| 2 | BonAlive® 1.0-2.0 | Granule size 1.0-2.0 mm, gamma sterilized |
| 3 | BonAlive® 2.0-3.15 | Granule size 2.0-3.15 mm, gamma sterilized |
| 4 | BonAlive® Putty | Paste like binder with BonAlive® granules (granule size 0.5-0.8 mm) + S53P4 spheres 0.09-0.425 mm), gamma sterilized |
| 5 | Putty 1 | Paste-like binder with 10% BonAlive® granules (granule size 90-125 µm) |
| 6 | Putty 2 | Paste-like binder with 10% BonAlive® granules (granule size 125-250 µm) |
| 7 | Putty 3 | Paste-like binder with 10% BonAlive® granules (granule size 250-315 µm) |
| 8 | Putty 4 | Paste-like binder with 20% BonAlive® granules (granule size 90-125 µm) |
| 9 | Putty 5 | Paste-like binder with 20% BonAlive® granules (granule size 125-250 µm) |
| 10 | Putty 6 | Paste-like binder with 20% BonAlive® granules (granule size 250-315 µm) |
| 11 | S53P4 glass powder (positive control) | granule particle size <45 µm, gamma sterilized |
| 12 | Putty binder | Pure polymer (PEG-glycerol) material without granules, gamma sterilized |
| 13 | Tricalcium phosphate (TCP) | Reference material, gamma sterilized |
| 14 | Inert glass (non-bioactive reference) | littala clear glass, hot air sterilized, granule size not defined |

The compositions Putty 1 to Putty 6 were tested with *Staphylococcus epidermidis* and *Pseudomonas aeruginosa*, all the other compositions were tested for all the strains listed in Table 1.

In Vitro Testing (Comparative Examples 1-4, 11-14)

The bacteria were incubated (5 ml sterile test tubes, Becton Dickinson) together with different products in sterile tryptone soy broth (TSB, comprising enzymatic digest of casein, enzymatic digest of soybean meal, sodium chloride, dipotassium phosphate and dextrose). The concentrations of the products used in the study are listed in Table 3. Granules, reference materials and controls were weighted (Mettler A E 50) and mixed properly with 2 ml of TSB. Three replicates of each product except six replicates of putty product were weighted. Three replicates of putty product were incubated 2 hours at room temperature, after which TSB with dissolved polymer was replaced by new 2 ml batch of TSB. Finally bacteria inoculums (known amount determined by optical densitometry, Thermo GeneSys 20) were added to the mixture. Bacterial cultures without added products and pure TSB served as controls. The S53P4 powder acted as a positive control since it is known from earlier studies that a concentration of 100 mg/ml of powder is sufficient for efficient bacterial inhibition. The littala glass and tricalcium phosphate (TCP) were included as reference materials. The inert littala non-bioactive glass was ground to small granules (exact granule size not defined) before the study.

TABLE 3

Product concentrations used in the study

| Product | Concentration (mg/ml) |
|---|---|
| BonAlive® 0.5-0.8 | 1000 |
| BonAlive® 1.0-2.0 | 1000 |
| BonAlive® 2.0-3.15 | 1000 |

TABLE 3-continued

Product concentrations used in the study

| Product | Concentration (mg/ml) |
|---|---|
| BonAlive ® Putty | 1400 |
| S53P4 glass powder | 100 |
| Putty binder | 560 |
| TCP | 600 |
| Iittala Glass | 600 |

The viability of the bacterial suspensions incubated with different products was assessed by using commercial, solid blood agar plates (Trypticase Soy Agar II with 5% Sheep Blood, Becton Dickinson). At consecutive 24 h cultivation points, 10 μL samples taken directly from the suspensions were plated (as described in Vuorenoja K, Jalava J, Lindholm L. et al. (2011) Detection of *Streptococcus pneumoniae* carriage by the Binax NOW test with nasal and nasopharyngeal swabs in young children. *Eur J Clin Microbial Infect*. EPub PMID: 21800217). In addition, one replicate of 1:10 000 dilutions of the samples and bacterial controls were plated to assure the quantifiable, single colony formation.

The growth of bacteria was evaluated by comparing to the control sample after cultivation (+37° C. for 16 h) on agar plates. Absence of growth on the plates was an indicator of the ability of a given product to prevent bacterial colonization. In vitro cultivation was carried out for a period of 7 days except for *P. aeruginosa* a period of 5 days could not be exceeded due the slime formation which prevented the accurate collection of a 10 μL sample.

pH of the samples was estimated from the test tubes by using pH paper (pH range 7.5-14 Merck Alkalit 81.09532 and range 6.4-8.0 Nacherey-Nagel, REF 90210). A piece of paper was dipped into broth after which pH value was estimated by comparing the color of the paper to scale provided by manufactures. pH estimation was done after 8 days cultivation for *S. aureus* and *S. epidermidis*, after 7 days for MRSA and 5 days for *P. aeruginosa*.

In Vitro Testing (Comparative Examples 5-10)

One strain of *Staphylococcus epidermidis* and one strain of *Pseudomonas aeruginosa* were used. Conditioning was obtained through the incubation of each product (final concentration 400 mg/ml) in growth medium for 48 hours at 37° C. pH values were measured at regular intervals. A pH value equal or higher than 10 was considered suggestive of optimal conditioning.

Antibacterial activity was evaluated by means of killing curves. An aliquot of bacterial suspension was inoculated into test tubes containing conditioned products. Growth controls were performed inoculating bacteria into growth medium alone. Tubes were incubated at 37° C. in aerobic atmosphere. Microbial counts were performed after 0, 24, 48 and 72 hours of incubation by plating a proper dilution of bacterial suspension on agar plates, which were incubated for 24 hours at 37° C.

Results of the Reference Materials (Comparative Examples)

Comparative Examples 1-4, 11-14

Negative controls gave consistently a result too numerous to count after plating. This was seen with all strains and at all time points which showed that the bacteria were viable throughout the study period. Pure TSB without an inoculant was used as a control to demonstrate that all work was performed aseptically. There was no bacterial growth in pure TSB at any of the time points.

All BonAlive® granules products tested (alone) affected bacterial growth. The time and level needed for the effect varied depending on the granule size. The effect also varied between bacterial species. The powder sieved to a particle size of <45 μm was able to resist the growth of all studied bacteria. The BonAlive® putty product did not affect the growth of any of the pathogens studied. *S. epidermidis, S. aureus* MetR and *P. aeruginosa* results showed a scarce effect in the middle of test period, but BonAlive® putty had no effect on *S. aureus* ATCC 29213. Day-to-day variations during the test period existed. Pure polymer (putty binder) had some effect on *S. epidermidis* and *S. aureus* MetR in the end of test period but day-to-day variations in growth existed. TCP had no effect in any day on gram negative *P. aeruginosa*, neither had it effect on *S. aureus* ATCC 29213 at the end of the test period. Slight effects on the two other gram positive cocci was observed.

In can thus be concluded that the BonAlive® putty product was not able to prevent the colonization of four clinically important pathogens during this test period. The day-to-day variation and shifty results of the putty and polymer may at least partly be explained by in vitro test setting used. In addition, the physical and chemical features of polymer might have some effect on pipetting quality.

All results of the bacterial growth are listed in Tables 4-7. The numbers listed indicate the difference ($\log_{10}$) between bacterial control and bacteria incubated with a sample (0=no difference to bacterial control, 1=$\log_{10}$ difference to bacterial control, 5 is a difference or more than 4 logs), 0 meaning no inhibition of the bacterial growth.

TABLE 4

S epidermidis

| S epidermidis | Day 1 | Day 2 | Day 3 | Day 4 | Day 5 | Day 6 | Day 7 |
|---|---|---|---|---|---|---|---|
| BonAlive ® 0.5-0.8 | 0 | 0 | 0 | 0 | 1 | 2 | 3 |
| BonAlive ® 1.0-2.0 | 0 | 0 | 0 | 0 | 1 | 2 | 3 |
| BonAlive ® 2.0-3.15 | 0 | 0 | 0 | 1 | 1 | 2 | 3 |
| BonAlive ® Putty | 0 | 0 | 1 | 1 | 1 | 0 | 0 |
| S53P4 glass powder | 5 | 5 | 5 | 5 | 5 | 5 | 5 |
| Putty binder | 0 | 0 | 0 | 0 | 1 | 1 | 1 |
| TCP | 0 | 0 | 1 | 1 | 0 | 1 | 1 |
| Iittala Glass | 0 | 0 | 0 | 0 | 0 | 2 | 0 |

TABLE 5

S. aureus

| S. aureus | Day 1 | Day 2 | Day 3 | Day 4 | Day 5 | Day 6 | Day 7 |
|---|---|---|---|---|---|---|---|
| BonAlive ® 0.5-0.8 | 0 | 0 | 0 | 1 | 1 | 2 | 3 |
| BonAlive ® 1.0-2.0 | 0 | 0 | 0 | 1 | 1 | 2 | 5 |
| BonAlive ® 2.0-3.15 | 0 | 0 | 0 | 1 | 1 | 2 | 3 |

TABLE 5-continued

| S. aureus | Day 1 | Day 2 | Day 3 | Day 4 | Day 5 | Day 6 | Day 7 |
|---|---|---|---|---|---|---|---|
| BonAlive ® Putty | 0 | 0 | 0 | 0 | 0 | 0 | 0 |
| S53P4 glass powder | 1 | 1 | 1 | 3 | 2 | 4 | 4 |
| Putty binder | 0 | 0 | 0 | 0 | 0 | 0 | 0 |
| TCP | 0 | 1 | 0 | 1 | 0 | 0 | 0 |
| Iittala Glass | 0 | 0 | 0 | 0 | 0 | 0 | 0 |

TABLE 6

| S. aureus MetR | Day 1 | Day 2 | Day 3 | Day 4 | Day 5 | Day 6 | Day 7 |
|---|---|---|---|---|---|---|---|
| BonAlive ® 0.5-0.8 | 0 | 0 | 1 | 2 | 2 | 5 | |
| BonAlive ® 1.0-2.0 | 0 | 0 | 0 | 1 | 2 | 5 | |
| BonAlive ® 2.0-3.15 | 0 | 0 | 0 | 2 | 3 | 3 | |
| BonAlive ® Putty | 0 | 0 | 0 | 1 | 0 | 0 | |
| S53P4 glass powder | 1 | 2 | 5 | 5 | 5 | 5 | |
| Putty binder | 0 | 0 | 0 | 1 | 0 | 0 | |
| TCP | 0 | 1 | 0 | 1 | 1 | 2 | |
| Iittala Glass | 0 | 0 | 0 | 0 | 0 | 0 | |

TABLE 7

| P. aeruginosa | Day 1 | Day 2 | Day 3 | Day 4 | Day 5 | Day 6 | Day 7 |
|---|---|---|---|---|---|---|---|
| BonAlive ® 0.5-0.8 | 0 | 0 | 1 | 2 | 2 | 5 | |
| BonAlive ® 1.0-2.0 | 0 | 0 | 0 | 2 | 3 | | |
| BonAlive ® 2.0-3.15 | 0 | 0 | 0 | | 5 | | |
| BonAlive ® Putty | 1 | | 1 | 0 | 0 | | |
| S53P4 glass powder | 1 | 3 | 5 | 5 | 5 | | |
| Putty binder | 0 | 0 | 0 | 0 | 0 | | |
| TCP | 0 | 0 | | 0 | 0 | | |
| Iittala Glass | 0 | 0 | 0 | 0 | 0 | | |

Table 8 summarises the pH values at the end of incubation period (8 days for *S. epidermidis* and *S. aureus,* 7 days for *S. aureus* MetR, 5 days for *P. aeruginosa*).

TABLE 8

| pH values | S. aureus | S. epidermidis | S. aureus MetR | P. aeruginosa |
|---|---|---|---|---|
| BonAlive ® 0.5-0.8 | 9.5 | 9.5 | 9.5 | 9.5 |
| BonAlive ® 1.0-2.0 | 9.5 | 9.5 | 9.5 | 9.5 |
| BonAlive ® 2.0-3.15 | 9.5 | 9.5 | 9.5 | 9.5 |
| BonAlive ® Putty | 6.8 | 8.5 | 7.8 | 6.8 |
| S53P4 glass powder | 10.0 | 10.0 | 9.5 | 10.0 |
| Putty binder | 6.4 | 6.4 | 6.4 | 6.4 |
| TCP | 8.0 | 7.4 | 8.0 | 8.0 |
| Iittala Glass | 8.5 | 7.8 | 7.8 | 8.5 |

Comparative Examples 5-10

Results for comparative examples 5-10 are shown in Table 9. The putty compositions showed a slight pH change (pH 8), but did not have an antimicrobial effect neither against *S. aureus* nor *P. aeruginosa*.

TABLE 9

Results for comparative examples 5-10

| | | Antimicrobial activity against | |
|---|---|---|---|
| Composition | pH after 48 hours | S. aureus | P. aeruginosa |
| Putty 1 | 8 | No | No |
| Putty 2 | 8 | No | No |
| Putty 3 | 8 | No | No |
| Putty 4 | 8 | No | No |
| Putty 5 | 8 | No | No |
| Putty 6 | 8 | No | No |

Antimicrobial Activity of the Paste According to the Invention

A paste having the composition indicated in Table 10 (composition 1) was tested for its antibacterial activity. Reference samples were a powder of bioactive glass with a fraction size of less than 45 µm (composition 2) and granules of bioactive glass with a fraction size of 500-800 µm (composition 3), gamma-sterilised as above.

Three samples of inert glass of similar size (R1350 Iittala clear, Iittala, Finland) were used as a negative control: granules of <45 µm with PEG and glycerol as indicated in Table 9 (Reference 1), granules of <45 µm (Reference 2) and granules of 500-800 µm (Reference 3). All samples were prepared at a final concentration of 400 mg/ml (corresponding to 5% of the clinical working solution) in Tryptic Soy Broth (TSB; Biomerieux, Marcy l'Etoile, France), and 4.8 ml of each solution were placed in sterile 6 well polystyrene microplates (Jet Biofil; Guangzhou, China). The bioactive glass samples were incubated at 37° C. for 4 hours for composition 1, 7 hours for composition 2 and 24 hours for composition 3. pH values were measured with a pH-meter at regular intervals to determine ions release and pH changes suggestive for conditioning. A pH value equal or higher of 11 was considered suggestive of optimal conditioning. Once optimal conditioning was reached, the content of each well was ready to use.

TABLE 10

The composition of the inventive paste tested

| Material | Amount (g) |
|---|---|
| Glycerol | 16 |
| PEG 400 | 12.8 |
| PEG 1500 | 25.6 |
| PEG 3000 | 9.6 |
| S53P4 granules, 500-800 µm | 76.8 |
| S53P4 powder, <45 µm | 19.2 |

One strain of methicillin-resistant *S. aureus* and one of *P. aeruginosa* isolated at the Microbiology Laboratory of IRCCS Galeazzi Orthopaedic Institute from infected knee prostheses of patients referring to the Center for Reconstructive Surgery of Osteoarticular Infections (C.R.I.O.) of the same Institute for implants revision were used. These strains were selected in function of their strong ability to in vitro produce biofilm on prosthetic materials.

Sterile sandblasted titanium disks with a diameter of 25 mm and a thickness of 5 mm (Adler Ortho, Cormano (Milan), Italy; BATCH J04051) were used as substrate for biofilm formation and growth. Overnight cultures of *S. aureus* and *P. aeruginosa* were resuspended at a final density of $1.0 \times 10^8$ CFU/ml in TSB and aliquots (200 µl) of each working solution were inoculated into 6 well polystyrene microplates containing titanium disks and 4.8 ml of fresh TSB. After incubation for 24 h at 37° C. aerobically, the exhausted growth medium containing non-adherent bacteria was removed and replaced with 5 ml of fresh medium. Plates were incubated for further 48 h to obtain a mature biofilm, then the medium and the remaining non-adhering bacteria, if present, were removed by washing three times with sterile saline.

After the conditioning time, titanium disks covered by bacterial biofilm were placed in new sterile 6 well polystyrene microplates containing either the conditioned bioglass or the negative control (inert glass). The amount of biofilm on each titanium disk was evaluated after 24, 48 and 72 hours of incubation.

Crystal Violet Assay

Crystal Violet assay was used as a preliminary test in order to assess the best formulation and the best incubation time of S53P4 glass to use against *S. aureus* and *P. aeruginosa* biofilms. To evaluate the effect of the tested glasses on the biofilm architecture, the whole biomass present on each disk was measured after treatment as described by Christensen et al. (Christensen G D, Simpson W A, Younger J J, et al. Adherence of coagulase-negative staphylococci to plastic tissue culture plates: a quantitative model for the adherence of staphylococci to medical devices. *J. Clin. Microbiol.* 22(6), 996-1006 (1985)). At the end of the incubation time, biofilm grown on titanium disks was air dried and stained by disk immersion in a 5% Crystal Violet solution for 15 minutes. Then, after several washings, the disks were air dried again, and placed in 3 ml of 96% ethanol to elute the Crystal Violet bound to biofilm. Three aliquots (100 µl) of each ethanol-dye solution were placed in a 96 multiwell plate and the absorbances were read at 595 nm with a microplate reader (Multiskan F C, Thermo Scientific; Milan, Italy) in triplicate for each disk.

Statistical Analysis

Biofilm amounts as measured by the Crystal Violet assay are presented as mean±SD. Statistical analysis was performed by means of Two way ANOVA followed by Bonferroni t-test and Student's t-test as appropriate. The limit of significance for P values was set at less than 0.05.

Results

The antibiofilm activity of S53P4, as the absorbance value at 595 nm for the two bacteria, is shown in Tables 11 and 12. The amount of biofilm present on all titanium disks after treatment was significantly different (P<0.05) between S53P4 treated disks and inert glass treated disks (controls). Although the time of exposure to bioactive glass seemed not to significantly affect the amount of biofilm, after 72 hours of treatment a reduction in biofilm was observed, in comparison to those observed after 24 and 48 hours. Anti-biofilm activity of S53P4 did not significantly differ among the three formulations tested.

TABLE 11

Absorbance at 595 nm for *S. aureus* MetR

| *S. aureus* MetR | 24 hours | 48 hours | 72 hours |
|---|---|---|---|
| Composition 1 | 0.8 | 0.6 | 0.4 |
| Composition 2 | 0.9 | 0.6 | 0.5 |
| Composition 3 | 0.9 | 0.6 | 0.5 |
| Reference 1 | 2.6 | 3.0 | 3.5 |
| Reference 2 | 3.8 | 3.8 | 3.9 |
| Reference 3 | 3.3 | 3.5 | 3.7 |

TABLE 12

Absorbance at 595 nm for *P. aeruginosa*

| *P. aeruginosa* | 24 hours | 48 hours | 72 hours |
|---|---|---|---|
| Composition 1 | 1.6 | 0.8 | 0.7 |
| Composition 2 | 1.5 | 0.7 | 0.5 |
| Composition 3 | 1.5 | 0.7 | 0.4 |
| Reference 1 | 3.5 | 3.8 | 3.9 |
| Reference 2 | 3.4 | 3.7 | 3.9 |
| Reference 3 | 3.2 | 3.7 | 3.8 |

The results thus show that irrespective of the antimicrobial activity of the bioactive glass itself, when it is mixed with glycol and PEG's, it does not have an antibacterial effect unless it is used in the form of a powder having a size distribution of 0.5-45 µm. Hence the combination of the teaching of EP 2322134 and the fact that this kind of bioactive glass powder has antimicrobial activity would not have been obvious to a person skilled in the art, since this is the only form of bioactive glass (i.e. the powder) that does have this surprising effect.

The invention claimed is:
1. An antibacterial, implantable paste comprising
   (a) bioactive glass powder having a size distribution of 0.5-45 µm in an amount of 10-30 wt-% of the total weight of the bioactive glass,
   (b) bioactive glass granules having a size distribution between 100 and 4000 um in an amount of 90-70 wt-% of the total weight of the bioactive glass,
   (c) low molecular weight polyethylene glycol having a molecular weight range of 200-700 g/mol,
   (d) medium molecular weight polyethylene glycol having a molecular weight range of 700-2500 g/mol,
   (e) high molecular weight polyethylene glycol having a molecular weight range of 2500-8000 g/mol and
   (f) glycerol,
   wherein the composition of the bioactive glass is 45-55 weight-% of $SiO_2$, 20-25 weight-% of $Na_2O$, 18-25 weight-% of CaO and 3-6 weight-% of $P_2O_5$, with the proviso that the molecular weight of the low molecular weight polyethylene glycol and of the medium molecular weight polyethylene glycol differ from each other by at least 80 g/mol and that the molecular weight of the medium molecular weight polyethylene glycol and of the high molecular weight polyethylene glycol differ from each other by at least 300 g/mol;
   wherein said implantable paste is antibacterial in the absences of an antibiotic;
   wherein the total amount of bioactive glass is 50-79 wt-% of the total weight of the paste;
   wherein the amount of low molecular weight polyethylene glycol having a molecular weight range of 200-700 g/mol (c) is 2-15 wt-% of the total weight of the paste, the amount of medium molecular weight polyethylene glycol having a molecular weight range of 700-2500 g/mol (d) is 8-47 wt-% of the total weight of the paste and the amount of high molecular weight polyethylene glycol (e) is 1-10 wt-% of the total weight of the paste;

wherein the total amount of polyethylene glycols is 20-50 wt-% of the total weight of the paste and that the amount of glycerol (f) is up to 10 wt-% of the total weight of the paste; and wherein the implantable bone paste does not comprise bioactive glass powder and bioactive glass granules that are spheres.

2. The paste according to claim 1, further comprising
(g) therapeutically active agent.

3. The paste according to claim 1, wherein said bioactive glass granules (b) have a size distribution of 125-315 μm.

4. The paste according to claim 1, wherein said bioactive glass granules (b) have a size distribution of 315-500 μm.

5. The paste according to claim 1, wherein said bioactive glass granules (b) have a size distribution of 500-800 μm.

6. The paste according to claim 1, wherein said bioactive glass granules (b) have a size distribution of 1000-2000 μm.

7. The paste according to claim 2, wherein the amount of therapeutically active agent (g) is up to 30 wt-% of the total weight of the paste.

8. The paste according to claim 1, wherein the composition of the bioactive glass is 45-54 weight-% of $SiO_2$, 22-25 weight-% of $Na_2O$, 19-25 weight-% of CaO and 3.5-6 weight-% of $P_2O_5$.

9. The paste according to claim 8, wherein the composition of the bioactive glass is 53 weight-% of $SiO_2$, 23 weight-% of $Na_2O$, 20 weight-% of CaO and 4 weight-% of $P_2O_5$ or 45 weight-% of $SiO_2$, 24.5 weight-% of $Na_2O$, 24.5 weight-% of CaO and 6 weight-% of $P_2O_5$.

10. An implant coated with a paste according to claim 1.

* * * * *